(12) United States Patent
Affolter et al.

(10) Patent No.: US 9,486,004 B2
(45) Date of Patent: Nov. 8, 2016

(54) MILK-BASED PROTEIN HYDROLYSATES AND INFANT FORMULAE AND NUTRITIONAL COMPOSITIONS MADE THEREOF

(75) Inventors: Michael Affolter, Savigny (CH); Isabelle Bureau-Franz, Paris (FR); Francoise Maynard, Spiegel Bei Bern (CH); Annick Mercenier, Bussigny (CH); Alexandre Panchaud, Lausanne (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 13/877,282

(22) PCT Filed: Sep. 30, 2011

(86) PCT No.: PCT/EP2011/067096
§ 371 (c)(1),
(2), (4) Date: Apr. 1, 2013

(87) PCT Pub. No.: WO2012/042013
PCT Pub. Date: Apr. 5, 2012

(65) Prior Publication Data
US 2014/0004152 A1    Jan. 2, 2014

(30) Foreign Application Priority Data
Oct. 1, 2010 (EP) .................... 10186222

(51) Int. Cl.
| | |
|---|---|
| C12N 9/52 | (2006.01) |
| A23J 3/34 | (2006.01) |
| A23L 1/29 | (2006.01) |
| A23L 1/305 | (2006.01) |
| A61K 38/01 | (2006.01) |
| A61K 39/35 | (2006.01) |
| A23C 9/152 | (2006.01) |

(52) U.S. Cl.
CPC ............ *A23L 1/296* (2013.01); *A23J 3/343* (2013.01); *A23J 3/344* (2013.01); *A23L 1/3053* (2013.01); *A23L 1/3056* (2013.01); *A61K 38/018* (2013.01); *A61K 39/35* (2013.01); *C12N 9/52* (2013.01); *A23C 9/1526* (2013.01); *A23V 2002/00* (2013.01)

(58) Field of Classification Search
None
See application file for complete search history.

(56) References Cited

U.S. PATENT DOCUMENTS

| | | |
|---|---|---|
| 2002/0037357 A1 | 3/2002 | Fritsche et al. |
| 2005/0058747 A1 | 3/2005 | Lassen et al. |
| 2010/0255153 A1* | 10/2010 | Oestergaard et al. .......... 426/42 |

FOREIGN PATENT DOCUMENTS

| | | | |
|---|---|---|---|
| DK | WO 2009062942 A2 * | 5/2009 | ............ C07K 1/22 |
| JP | 6343422 | 12/1994 | |
| JP | 2000063284 | 2/2000 | |
| WO | 2004072279 | 8/2004 | |
| WO | WO2010073039 | 7/2010 | |
| WO | WO2010112546 | 10/2010 | |

OTHER PUBLICATIONS

English-language machine translation for JP 06-343422 published Dec. 20, 1994.*
Russian Office Action for Application No. 2013120283, dated Oct. 1, 2015, 4 pages.

* cited by examiner

*Primary Examiner* — Robert Mondesi
*Assistant Examiner* — Todd M Epstein
(74) *Attorney, Agent, or Firm* — K&L Gates LLP

(57) ABSTRACT

A composition including protein hydrolysates derived from milk is obtained by the treatment of enzymes derived from microorganisms. A trypsin-like enzyme and a chemotrypsin-like enzyme are used. The composition is in particular intended for inducing tolerance in infants with the effect of modulating the potential occurrence of allergies later in life. The composition can also be used in sick adult patients. Preferably the composition is an infant formula, infant follow-up formula, growing-up milk or baby food or an enteral complete nutritional composition.

6 Claims, 13 Drawing Sheets

SEQUENCE LISTING

```
<160> NUMBER OF SEQ ID NOS: 2

<210> SEQ ID NO 1
<211> LENGTH: 225
<212> TYPE: PRT
<213> ORGANISM: Kutzneria albida

<400> SEQUENCE: 1

Ile Val Gly Gly Thr Lys Ala Ser Thr Ser Thr Tyr Pro Phe Val Val
1               5                   10                  15

Phe Leu Thr Asp Ser Thr Gly Phe Gln Phe Cys Gly Gly Thr Leu Val
                20                  25                  30

Lys Pro Asn Lys Val Val Thr Ala Ala His Cys Thr Val Gly Glu Ser
            35                  40                  45

Ala Ala Asn Ile Arg Val Val Ala Gly Arg Asp Asp Lys Gln Ser Thr
        50                  55                  60

Ala Gly Thr Val Ser Lys Val Ser Lys Ile Trp Ile His Pro Ser Tyr
65                  70                  75                  80

Gln Asp Ala Thr Lys Gly Ser Asp Val Ser Val Leu Thr Leu Ser Thr
                85                  90                  95

Ser Leu Thr Gln Phe Thr Pro Leu Pro Leu Ala Ala Thr Thr Asp Thr
                100                 105                 110

Ala Leu Tyr Lys Glu Gly Thr Ala Ala Thr Ile Leu Gly Trp Gly Asp
            115                 120                 125

Thr Thr Glu Gly Gly Ser Ala Ser Arg Tyr Leu Leu Lys Ala Thr Val
        130                 135                 140

Pro Leu Thr Ser Asp Ala Thr Cys Lys Lys Ala Tyr Gly Glu Tyr Ser
145                 150                 155                 160

Ser Thr Ala Met Val Cys Ala Gly Tyr Pro Gln Gly Gly Thr Asp Thr
                165                 170                 175

Cys Gln Gly Asp Ser Gly Gly Pro Leu Val Ala Gly Asn Lys Leu Ile
            180                 185                 190

Gly Ile Thr Ser Trp Gly Gln Gly Cys Ala Glu Ala Gly Tyr Pro Gly
        195                 200                 205

Val Tyr Thr Arg Val Ala Thr Tyr Ser Ser Leu Ile Thr Gln Gln Leu
    210                 215                 220

Gly
225

<210> SEQ ID NO 2
```

```
<211> LENGTH: 375
<212> TYPE: PRT
<213> ORGANISM: Brachysporiella gayana

<400> SEQUENCE: 2

Met Glu Leu Thr Ser Leu Ile Ala Ala Leu Ala Val Ile Leu Pro Ile
1               5                   10                  15

Ala Tyr Gly Val Pro Met Asp Ala Thr Thr Asn Leu Ser Pro Lys Val
            20                  25                  30

Leu Ala Ala Met Lys Arg Asp Leu Gly Leu Asp Ala Arg Glu Ala Thr
        35                  40                  45

Ala Arg Val Thr Phe Glu Arg Arg Ala Gly Asp Val Ile Glu Glu Leu
    50                  55                  60

Arg Ser Ser Leu Gly Asp Ser Phe Ala Gly Ala Trp Val Thr Asp Gly
65                  70                  75                  80

Lys Val Ile Asn Ile Gly Val Thr Asp Gln Ala Leu Val Ser Lys Val
                85                  90                  95

Lys Glu Ala Gly Ala Glu Pro Met Val Met Lys Asn Ser Leu Gly Lys
            100                 105                 110

Leu Gln Glu Ala Lys Lys Lys Leu Asp Gln Ile Ile Lys Glu Lys Pro
        115                 120                 125

Lys Thr Leu Ser Thr Ser Gly Lys Pro Gly Ile Ala Thr Tyr Tyr Val
    130                 135                 140

Asp Ile Glu Thr Asn Lys Leu Ile Ile Thr Ala Leu Ser Thr Ser Ile
145                 150                 155                 160

Thr Gln Ala Glu Asp Leu Ala Lys Glu Val Gly Leu Ser Glu Ser Glu
                165                 170                 175

Phe Glu Val Arg Lys Thr Glu Lys Met Pro Ser Pro Phe Ile Leu Gly
            180                 185                 190

Gly Asp Pro Phe Val Ile Asn Asn Ser Ala Val Cys Ser Val Gly Phe
        195                 200                 205

Ala Val Ser Gly Gly Phe Val Ser Ala Gly His Cys Gly Gly Gln Gly
    210                 215                 220

Ser Pro Val Thr Tyr Ile Asp Gly Gly Ala Leu Gly Thr Ile Glu Gly
225                 230                 235                 240

Ser Val Phe Pro Gly Asp Ala Asp Met Ser Phe Ile Arg Ala Val Asp
                245                 250                 255

Gly Thr Asp Leu Pro Gly Ile Val Gly Thr Tyr Gly Asn Gly Asp Gln
            260                 265                 270

Pro Ile Phe Gly Ser Asn Val Ala Pro Ile Gly Ser Gly Val Cys Arg
        275                 280                 285

Ser Gly Thr Thr Thr Gly Tyr His Cys Gly Gln Leu Asp Ala Tyr Asp
    290                 295                 300

Val Thr Val Asn Tyr Asp Val Gly Pro Val Phe Gly Leu Thr Met Thr
305                 310                 315                 320

Ser Ala Cys Ala Glu Pro Gly Asp Ser Gly Ser Phe Phe Ala Gly
                325                 330                 335

Asp Gln Ala Gln Gly Val Thr Ser Gly Gly Ser Gly Asp Cys Thr Ser
            340                 345                 350

Gly Gly Gln Thr Phe Phe Gln Pro Val Asn Glu Ile Leu Glu Thr Tyr
        355                 360                 365

Gly Leu Ser Leu Thr Thr Ala
    370                 375
```

MILK-BASED PROTEIN HYDROLYSATES AND INFANT FORMULAE AND NUTRITIONAL COMPOSITIONS MADE THEREOF

CROSS REFERENCE TO RELATED APPLICATIONS

The present application is a National Stage of International Application No. PCT/EP2011/067096, filed on Sep. 30, 2011, which claims priority to European Patent Application No. 10186222.5, filed Oct. 1, 2010, the entire contents of which are being incorporated herein by reference.

REFERENCE TO SEQUENCE LISTING

This application contains a Sequence Listing in computer readable form. The computer readable form is incorporated herein by reference.

FIELD OF THE INVENTION

The present invention relates to compositions comprising a milk-based protein hydrolysate obtainable by treatment of a solution of a milk-based proteinaceous material with enzymes from a microbial source. The compositions may be incorporated into infant formulas and adult food supplements. The invention concerns the two different types of protein hydrolysates aimed at allergy prevention and allergy treatment. In the first case, infants are healthy, but at risk of allergy because of history of allergies in the family. In the second case, infants or adults are allergic or in needs, hence sick.

BACKGROUND OF THE INVENTION

Human Breast Milk and breast feeding represent the uncontested gold standard in terms of infant nutrition. Infant formulae that serve as a substitute for or complement to human breast milk should satisfy the nutritional requirements of infants, have an acceptable taste and be hypoallergenic and tolerogenic (i.e. able to induce oral tolerance) when targeted to infants at risk of allergy. Induction of oral tolerance to cow's milk has been described in EP0827697. It is known that allergies to cows' milk and to infant formulae containing cow's milk protein are due to the fact that the proteins of cows' milk differ from the proteins of mother's milk and can constitute allergens for humans. The principal recognized cow's milk allergens are alpha-lactalbumin (aLA), beta-lactolglobulin (bLG) and bovine serum albumin (BSA). Bovine whey protein and/or casein are often used as the milk protein source in infant formulae. To reduce allergenicity, cow's milk proteins are hydrolysed by enzymes and thus reduced to peptides. Current hypoallergenic formulas composed of such cow's milk proteins hydrolysates aimed at allergy prevention also comprise other nutrients such as animal oils, vegetable oils, starch, maltodextrin, lactose and sucrose. These protein hydrolysates may also be incorporated into an adult milk drink or food supplements.

The hydrolysis process used to produce these hydrolysates must be carefully monitored so that the final product hydrolysate retains its nutritional value and desired physical properties but is hypoallergenic and tolerogenic.

Hydrolysates may be characterised as "partial" or "extensive" depending on the degree to which the hydrolysis reaction is carried out. Currently there is no agreed legal/clinical definition of Extensively Hydrolyzed Products according to the WAO (World Allergy Organization) guidelines for Cow's milk protein allergy (CMA) but there is agreement that according to the WAO that hydrolyzed formulas have proven to be a useful and widely used protein source for infants suffering from CMA. In the current invention a partial hydrolysate is in one in which 60% of the protein/peptide population has a molecular weight of less than 1000 Daltons, whereas an extensive hydrolysate is one in which at least 95% of the protein/peptide population has a molecular weight of less than 1000 Daltons. These definitions are currently used in the industry. Partial hydrolysates are considered as hypoallergenic (HA) whereas extensive hydrolysates are considered as non allergenic.

Many groups have carried out research in order to optimise the hydrolysis process. Hydrolysis reaction conditions including temperature and reactor volume, number of cycles of hydrolysis, choice of protein substrate, enzyme(s) type and concentration are some of the many factors that influence hydrolysis reaction and thus the physical, chemical and ultimately biological properties of the final product. In EP0353122, mixtures of trypsin and chymotrypsin with a ratio of the trypsin/chymotrypsin activities of 0.33 to 0.66 are used to prepare hypoallergenic whey protein hydrolysates. WO9304593 A1 and U.S. Pat. No. 5,039,532A also disclose a hydrolysis process using trypsin and chymotrypsin, which includes a two-step hydrolysis reaction with a heat denaturation step in between to ensure that the final hydrolysate is substantially free of intact allergenic proteins. The trypsin and chymotrypsin used in these methods are preparations produced by extraction of porcine pancreas. A number of products containing protein hydrolysates prepared based on these methods exist on the market. For example, a Nestlé HA® infant formula may be prepared with a hydrolysate produced using trypsin and chymotrypsin extracted from animal pancreas and its hypoallergenic characteristics have been well studied and documented. Three major papers have been published reporting the results of a large randomized and double-blind intervention study performed in Germany, the aim of which was to compare the effect of hydrolyzed formulas vs standard cow's milk formula for the prevention of allergic manifestations, especially atopic eczema, in at risk infants. The publication are listed as following. The effect of hydrolyzed cow's milk formula for allergy prevention in the first year of life: the German Infant Nutritional Intervention Study, a randomized double-blind trial. von Berg A, Koletzko S, Grübl A, Filipiak-Pittroff B, Wichmann H E, Bauer C P, Reinhardt D, Berdel D; German Infant Nutritional Intervention Study Group. J Allergy Clin Immunol. 2003 March; 111:533-40.

Certain hydrolyzed formulas reduce the incidence of atopic dermatitis but not that of asthma: three-year results of the German Infant Nutritional Intervention Study. von Berg A, Koletzko S, Filipiak-Pittroff B, Laubereau B, Grübl A, Wichmann H E, Bauer C P, Reinhardt D, Berdel D; German Infant Nutritional Intervention Study Group. J Allergy Clin Immunol. 2007 March; 119:718-25.

Preventive effect of hydrolyzed infant formulas persists until age 6 years: long-term results from the German Infant Nutritional Intervention Study (GINI Study). von Berg A, Filipiak-Pittroff B, Kramer U, Link E, Bollrath C, Brockow I, Koletzko S, Grübl A, Heinrich J, Wichmann H E, Bauer C P, Reinhardt D, Berdel D; GINIplus study group, J Allergy Clin Immunodol 2008; 121:1442-7.

The conclusion of the latter GINI study was that early nutritional intervention with Nestlé H.A. infant formula, NAN HA® in high-risk children has a long-term preventive effect on atopic dermatitis until the age of 6 years, indicating a real disease reduction rather than postponement of disease onset.

The long-term preventive effect meaning a preventive effect lasting far beyond the period of feeding Nan HA®, shows that oral tolerance was induced, although the immune mechanisms involved in this tolerance induction have not been examined in the GINI study.

As well as being hypoallergenic it would be highly desirable that the infant formula to be used as a complement to or substitute for breast milk has ability to induce oral tolerance in the infant. Oral tolerance is the specific suppression of cellular and/or humoral immune reactivity to an antigen by prior administration of the antigen by the oral route. It is an important part of the development of the immune system in the first months of life and allows the infant to consume food without adverse reaction. Failure of oral tolerance establishment leads to allergy. The development of oral tolerance is linked to the immune system education, ending up with reduced reaction to food antigens. It is believed that some peptides, that may be specifically present in partially hydrolyzed infant formula, have the ability to interact with the immune system and induce oral tolerance induction. It is believed that these peptides should have particular properties, including a relatively small size, to better support the education of the immune system without acting as allergens themselves. It is also believed that the sequences of the specific peptides may play a significant role. Specific hydrolysate peptidic profiles may actually be at the core of the induction of oral tolerance.

Currently there is a widespread trend to move away from the use of enzymes from animals towards the use of those from microbial sources. There has been much progress in the last 20 years in the area of enzyme production by genetic engineering. This has made it possible to reproducibly prepare large quantities of high quality, high purity enzyme in a relatively short space of time. For these reasons it would be desirable to be able to use enzymes from a microbial source for the production of milk protein hydrolysates to be used in hypoallergenic infant formula. Furthermore it would be highly desirable to that these milk protein hydrolysates have the ability to induce oral tolerance in infants.

Thus in order to retain the hypoallergenic properties of the mammalian enzyme derived hydrolysates those produced with microbial enzymes must possess similar chemical, physical and biological properties. Furthermore, any new infant formula on the market is submitted to strict regulatory guidelines, for example in Europe Directive 2006/141/EC applies. Thus, it is desirable that any new product has a very similar peptide profile to that of the already validated product made with mammalian enzymes in order to keep an allergy preventive effect. Furthermore, it would be highly desirable that these milk protein hydrolysates have the ability to induce oral tolerance in infants.

Similarly, it is desirable to promote the reduction of allergies or adverse effect, enhance the absorption of proteins or amino acid, favour the utilization of proteins or amino acids and/or modulate inflammation processes in sick patients, especially by providing particular hydrolysates of proteins in complete nutritional compositions There is a need for a hydrolysate of milk-derived proteins prepared by the action of non mammalian enzymes, preferably microbial enzymes that present low allergenicity while presenting the capacity of oral tolerance induction.

There is a need for such and hydrolysate to be preferably comprised in an infant formula and/or a nutritional composition that are targeted to individuals at risk of allergies.

There is a need for such compositions that reduce the risk or severity of allergies later in life and help modulating the occurrence of allergic symptoms.

There is a need for obtaining bacterial enzyme-based hydrolysates with peptidic profiles that share some similarities with hydrolysates obtained from mammalian enzyme and, even more so, that are able to reproduce the oral tolerance properties of the latter, with demonstrated prevention of allergic symptoms.

There is a need to use the same enzymes as above in the preparation of nutritional compositions for sick or fragile patients.

As well as producing "partial" hydrolysates these microbial enzymes can also be used to produce "extensive" protein hydrolysates present in therapeutic formulae, such as those intended to feed cow's milk allergic infants and children. In this case, the target population would be sick (allergic) infants and children that are already sensitized to cow's milk proteins.

Those microbial enzymes could also be used to produce any type of protein hydrolysates used in infant, child, or adult products targeting other benefits than those related to allergy, such as facilitated digestion, enhanced absorption and metabolisation of amino-acids, peptides and proteins, promoted recovery from sickness, optimized utilization of nitrogen sources, promotion of tissue build-up and energy reserve.

To address this problem, the inventors have carried out an extensive research programme, and have compared a number of microbial enzymes as potential candidates for carrying out the hydrolysis reaction. They monitored parameters including hydrolysis reaction performance, enzymes specificity and peptide molecular weight profile and have determined that a number of specific enzyme mixtures provide hydrolysates with the desired physical, chemical and biological properties. The milk protein hydrolysates disclosed herein may be produced efficiently and reproducibly, have an acceptable taste, have the required nutritional value and are hypoallergenic. Furthermore, the hydrolysates of the invention may induce oral tolerance.

SUMMARY OF THE INVENTION

The present invention concerns compositions comprising milk-based protein hydrolysates obtainable by treatment of a solution of a milk-based proteinaceous material with
   a) at least one trypsin-like endopeptidase produced from a microorganism, and
   b) at least one chymotrypsin-like endopeptidase produced from a microorganism.

As characterised by peptide molecular weight profile, peptide sequence profile (endopeptidase specificity), and the hydrolysis efficiency of the endopeptidases the hydrolysates of the invention have similar properties to those of the milk-based protein hydrolysates produced by mammalian enzymes.

The hydrolysates of the invention have therapeutic and preventive effects, and may be used especially for the induction of oral tolerance in infants or patients in need thereof, or for reducing the risk of allergies in infants or patients in need thereof, or for reducing the severity of allergies during infancy or later in life, especially in infants or patients in need thereof.

The hydrolysates may be incorporated into an infant starter formula, a follow-on formula, a baby food formula, an infant cereal formula or a growing-up milk, or an adult nutritional composition or an adult milk-protein based drink for individuals in need of therapy and preferably said composition is a starter infant formula.

In one aspect of the invention the at least one trypsin-like endopeptidase is derived from a strain of *Fusarium*, preferably *Fusarium oxysporum*, or from a strain of *Kutzneria*, preferably *Kutzneria albida*.

In another aspect of the invention the at least one chymotrypsin-like endopeptidase is derived from a strain of *Nocardiopsis*, preferably *Nocardiopsis* Sp. or *Metarhizium*, preferably *Metarhizium anisopliae*, or *Brachysporiella*, preferably *Brachysporiella gayana*.

In another aspect of the invention the ratio of the trypsin-like endopeptidase to the chymotrypsin-like endopeptidase, based on weight of enzyme, is in the range 5:1 to 35:1, preferably 20:1 to 30:1, more preferably 27:1.

In another aspect of the invention the ratio of the trypsin-like endopeptidase to the chymotrypsin-like endopeptidase is 9:1, based on weight of enzyme, when the trypsin-like endopeptidase is derived from the strain *Fusarium* and the chymotrysin-like endopeptidase is derived from the strain *Nocardiopsis*.

DETAILED DESCRIPTION OF THE INVENTION

Figure 1:
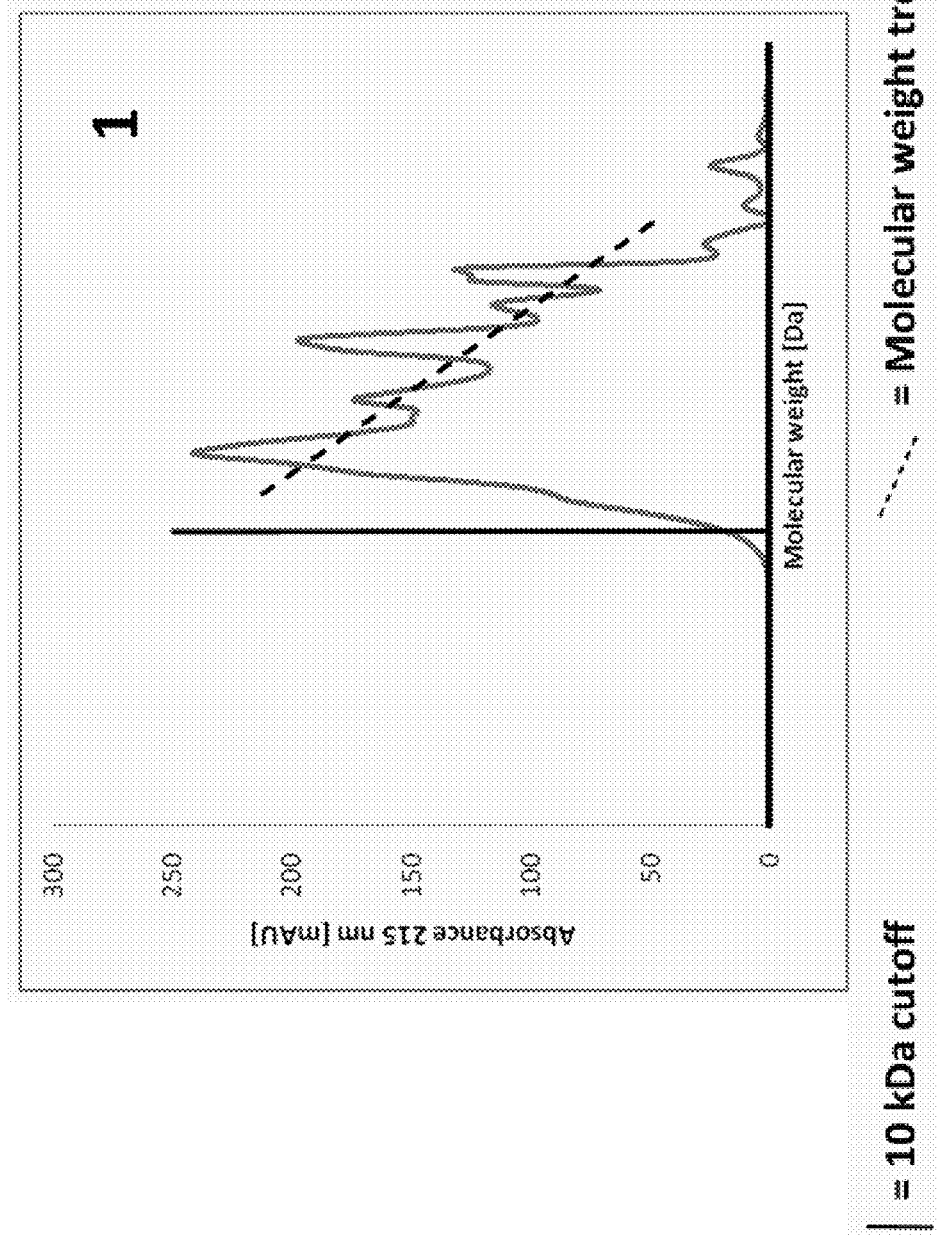
FIG. 1 Peptide size exclusion chromatography separation of the hydrolysates of Example 1. Peptides are separated based on their molecular weight (MW) using a size exclusion chromatography column (Superdex Peptide 10/300 GL from GE). Elution of the peptides is monitored by UV at 215 nm. Results show that the size distributions of combination 2, 4 and 6 are very close to the reference PTN (experiment 1, see text) as illustrated by the steep decrease from high to low molecular weight compared to combinations 3 and 5 for which a plateau is rather observed (See trendline). These results suggest that the enzymatic efficiency of experiment 2, 4 and 6 is generating a peptide population very similar in size while 3 and 5 are more enriched in smaller peptide compared to the reference.
Figure 1:
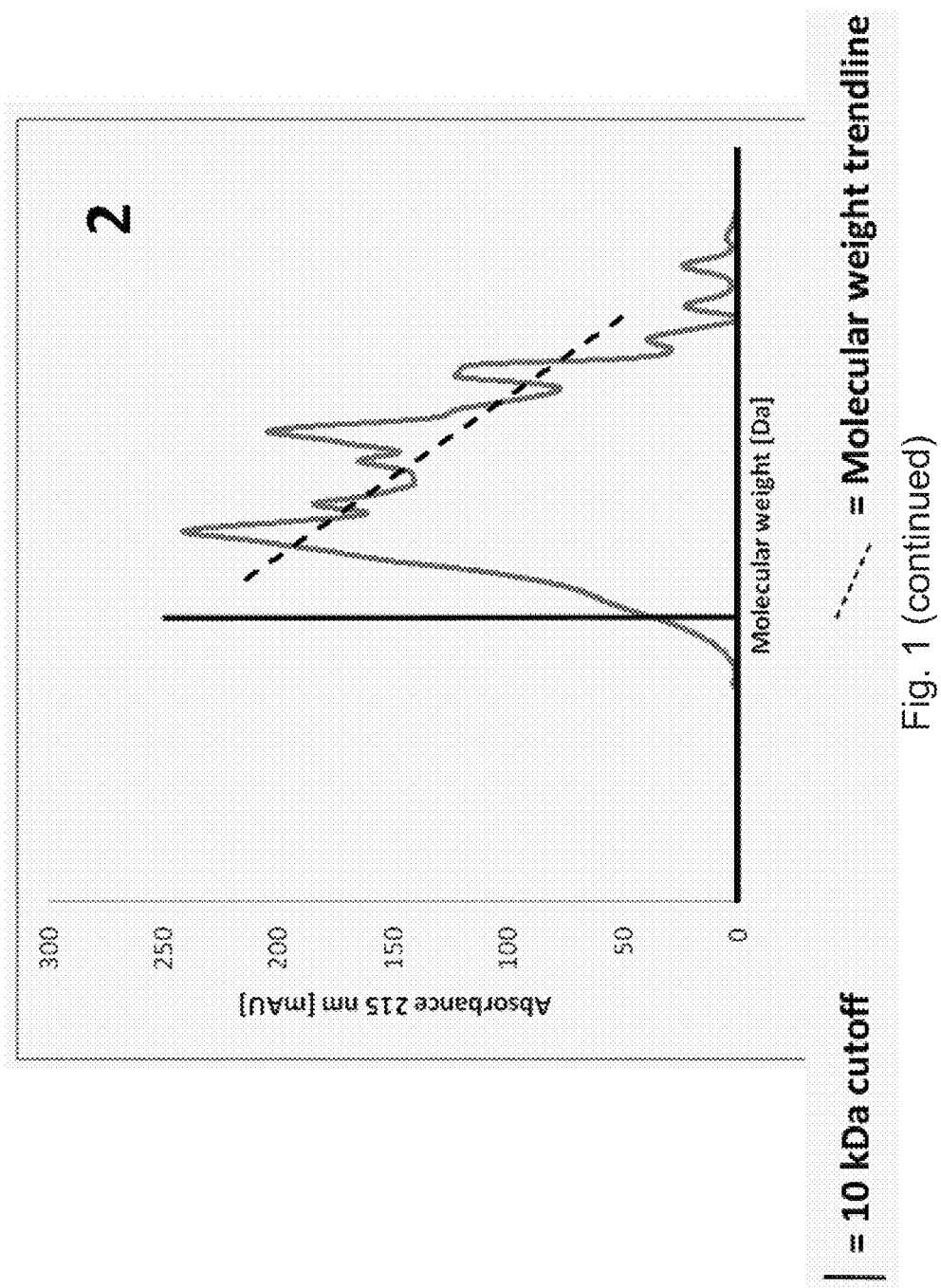
Figure 1:
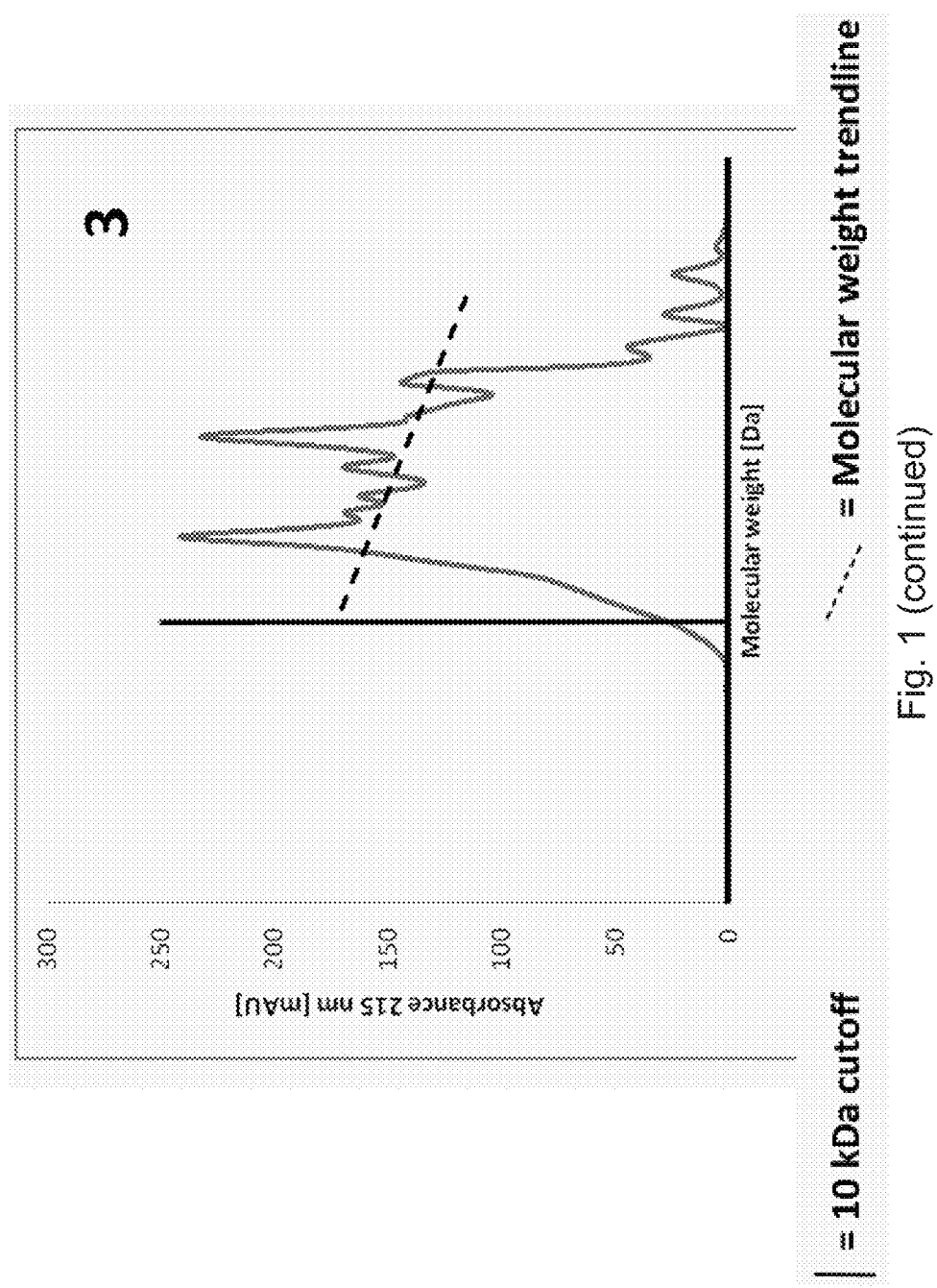
Figure 1:
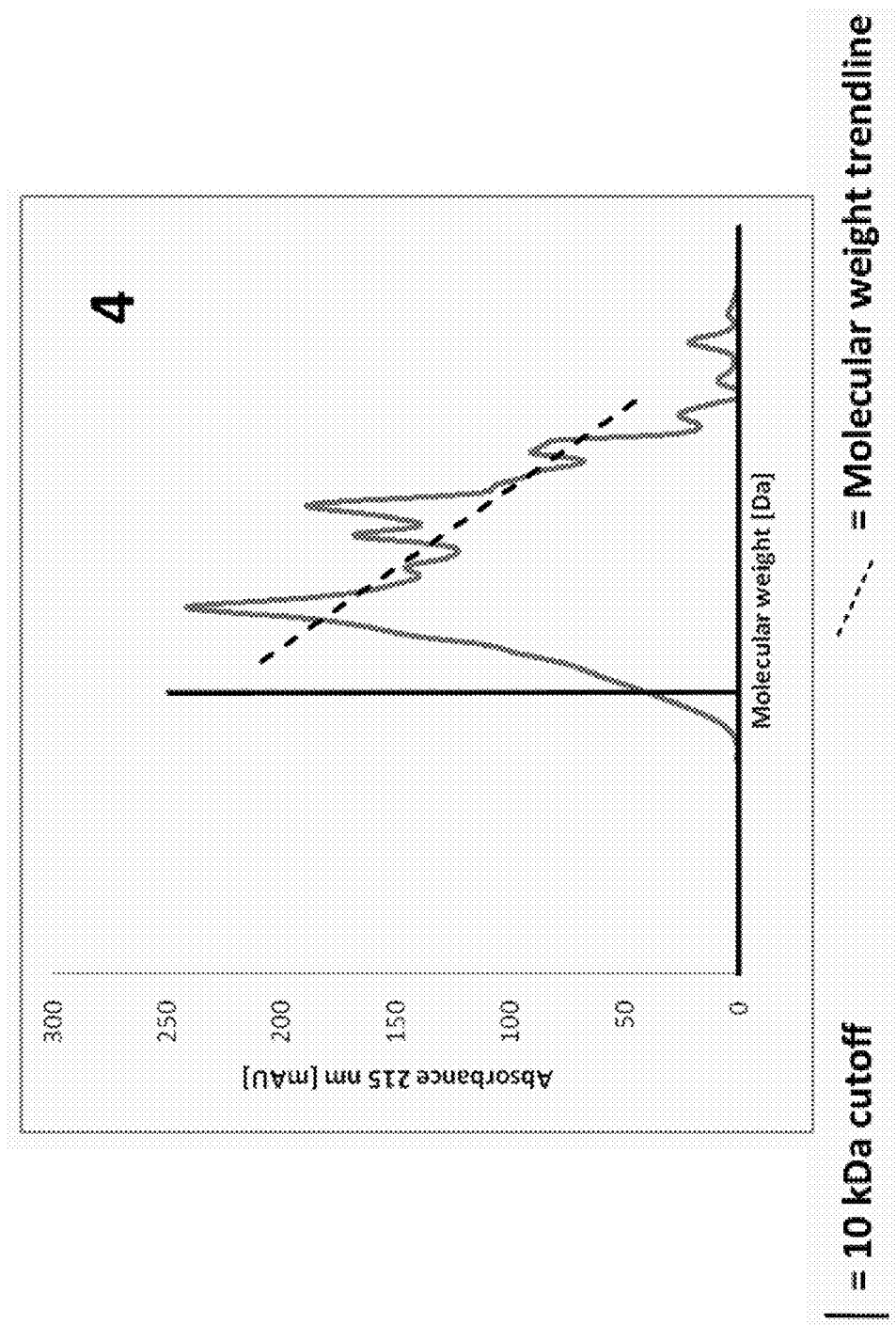
Figure 1:
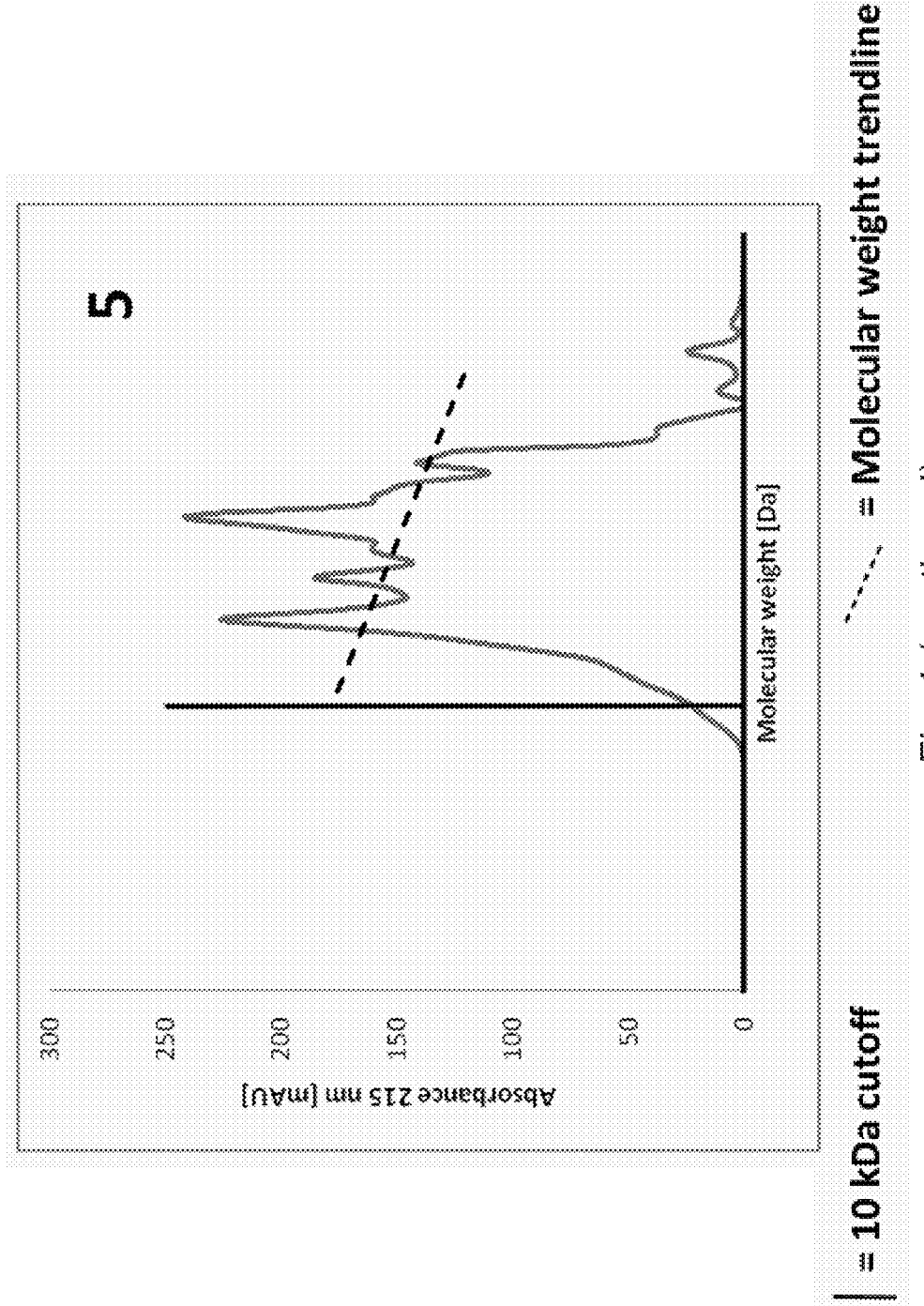
Figure 1:
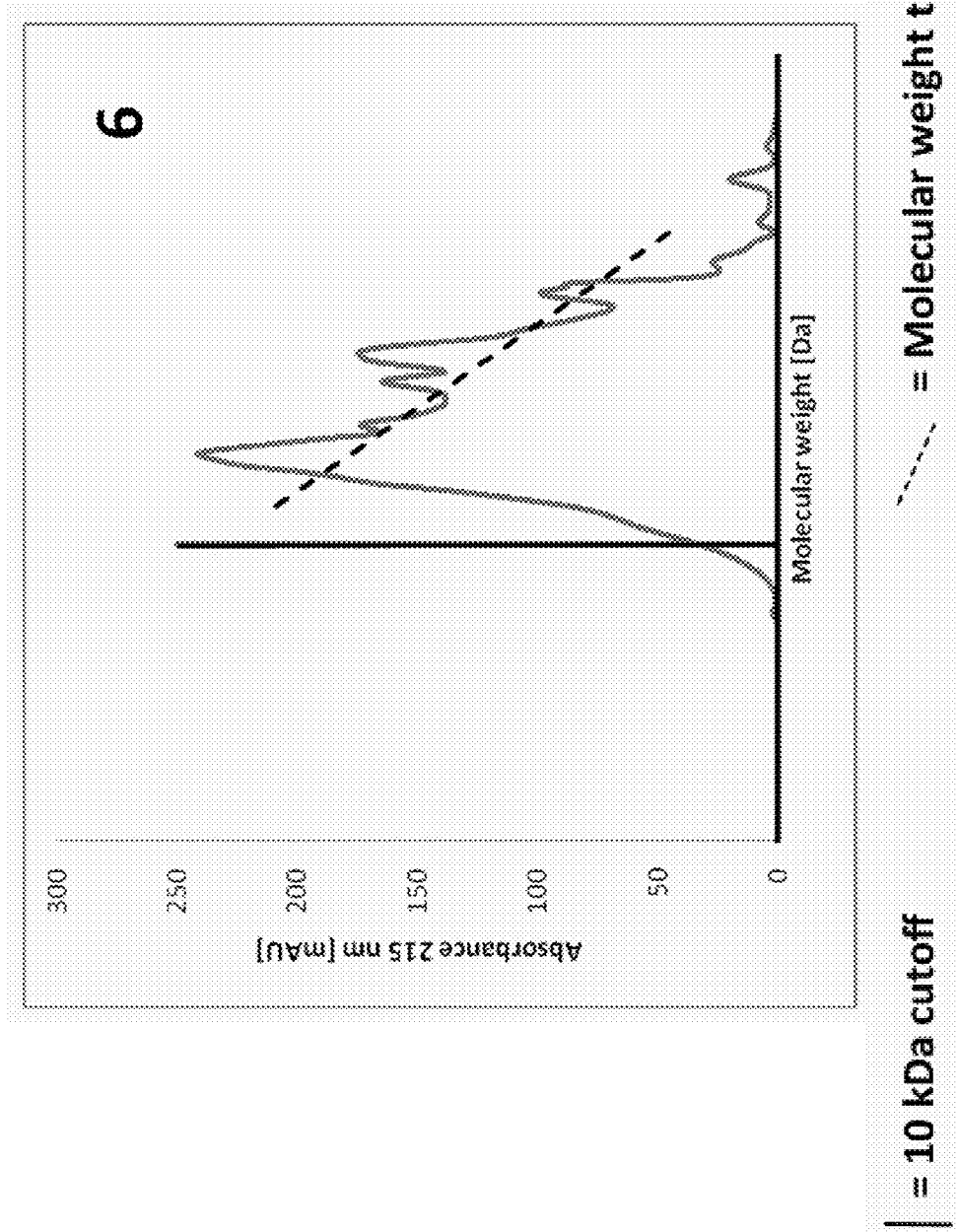

The milk-based protein hydrolysates of the current invention are obtained by the treatment of a solution of a milk-based proteinaceous material with a trypsin-like endopeptidase and a chymotrypsin-like endopeptidase from a microbial source.

Milk-Based Proteinaceous Material

In the compositions according to the invention the starting material is a milk-based proteinaceous material. It may be a whey-based proteinaceous material, casein or mixtures of whey-based proteinaceous material and casein. The casein source may be acid casein or non-fat milk solids. The whey based proteinaceous material may be a whey from cheese making, particularly a sweet whey such as that resulting from the coagulation of casein by rennet, an acidic whey from the coagulation of casein by an acid, or the acidifying ferments, or even a mixed whey resulting from coagulation by an acid and by rennet. This starting material may be whey that has been demineralized by ion exchange and/or by electrodialysis and is known as demineralised whey protein (DWP). In a preferred embodiment, the source of such whey-based proteinaceous material is sweet whey from which the caseino-glyco-macropeptide (CGMP) has been totally or partially removed. This is called modified sweet whey (MSW). Removal of the CGMP from sweet whey results in a protein material with threonine and trytophan contents that are closer to those of human milk. A process for removing CGMP from sweet whey is described in EP 880902.

The starting material may be a mix of DWP and MSW. It may be a concentrate of whey proteins 35-80% protein (WPC) or an isolate if the whey protein concentration is more than 95% protein (WPI). As example of WPC one can cite WPC 87 Lacprodan® available from Arla Foods, Denmark and as example of WPI one can cite Bipro® from Davisco Foods International (Minnesota USA).

The milk based proteinaceous material may be in solution or suspension, and is present at a concentration of 2-30% by weight of proteinaceous material, more preferably 5-20%, more preferably 6-10%.

The starting material may even be a combination of the above-mentioned starting materials and lactose. Lactose may be present as part of the whey protein concentrate or may be added. Addition of lactose to starting material for hydrolysis has the advantage that any residual protein contained in the lactose is hydrolysed. Lactose may be present in concentrations from 0.05-30% w/w, preferably 0.10-20% w/w, or in cases where a lower lactose content is preferred, 0.10 to 1%, preferably 0.10 to 0.20% (w/w). In the latter case the final product may be destined for infants or adults with a low lactose tolerance. Lactose may be removed, for example, by ultrafiltration (yielding UF whey), optionally followed by dialysis.

The starting material may be in the form of a true or colloidal aqueous solution, or in the form of a powder. In the latter case, the powder is dissolved in preferably demineralised water to form an aqueous solution.

Enzymes Produced by a Microorganism

The trypsin-like endopeptidase and chymotrypsin-like endopeptidase of the invention may be produced from a microorganism of any genus. Herein "produced from" is given to mean produced by fermentation of a cell of the given organism. The latter enzymes may be native to the organism from which they are produced or may be engineered into a host organism by insertion of the nucleotide sequence encoding the endopeptidase.

Trypsin-Like Endopeptidase:

Trypsin (EC 3.4.21.4) is a serine protease found in the digestive system of many vertebrates, where it hydrolyses proteins. It is produced in the pancreas as the inactive proenzyme trypsinogen. Trypsin cleaves peptide chains or links mainly at the carboxyl side of the amino acids lysine or arginine, except when either is followed by proline. By "trypsin-like endopeptidase" in the current invention, it is meant an enzyme that has an activity which resembles the activity of mammalian trypsin, e.g., trypsin extracted from porcine pancreatic tissue. By "trypsin-like endopeptidase" it is also meant an endopeptidase which preferentially cleaves peptides or proteins at the C-terminal side of the L-isomer of arginine and/or lysine, preferably arginine and lysine. The trypsin-like endopeptidase may be derived from a gram-positive bacterial strain such as *Bacillus, Clostridium, Enterococcus, Geobacillus, Kutzneria, Lactobacillus, Lactococcus, Oceanobacillus, Staphylococcus, Streptococcus,* or *Streptomyces* or a gram negative bacterial strain such as *Campylobacter, Escherichia* (preferably *E. coli*), *Flavobacterium, Fusobacterium, Helicobacter, Ilyobacter, Neisseria, Pseudomonas, Salmonella,* or *Ureaplasma,* or a fungal strain such as *Saccharomyces, Kluyveromyces, Pichia, Candida, Aspergillus, Penicillium, Fusarium,* and *Claviceps*. In a preferred embodiment, the trypsin-like endopeptidase is a fungal endopeptidase, preferably from a strain of *Fusarium,* more preferably *Fusarium oxysporum* which has the sequence registered under the name SWISSPROT No. P35049. The trypsin-like endopeptidase may have at least 75%, at least 80%, at least 85%, at least 90%, at least 95%, at least 96%, at least 97%, at least 98%, at least 99% or 100% sequence identity to SWISSPROT No. P35049. The enzyme coded by the latter sequence has been described (U.S. Pat. No. 5,288,627; U.S. Pat. No. 5,693,520).

In another preferred embodiment, the trypsin-like endopeptidase is derived from a gram positive bacterium, preferably a strain of *Kutzneria,* more preferably from *Kutzneria albida*. In another preferred embodiment, the trypsin-like endopeptidase has a sequence identity to the mature polypeptide of SEQ ID NO: 1 of at least 70%, at least 75%, at least 80%, at least 85%, at least 90%, at least 95%, at least 96%, at least 97%, at least 98%, at least 99%, or 100%.

The concentration of trypsin-like endopeptidase may be 100-500,000 USP Trypsin Units per g food protein, e.g., 250-250,000 or 500-100,000. One USP Trypsin Unit is the activity causing a change in absorbance at 253 nm of 0.003 at pH 7.6 and 25° C. using N-benzoyl-L-arginine ethyl ester hydrochloride (BAEE) as substrate.

Otherwise expressed in terms of mg of >95% pure enzyme protein/ml this means that the trypsin-like endopeptidase concentration can range from 0.5 to 4, preferably from 1 to 3.5, and more preferably 1.5 to 3 mg per g milk protein. This is independent of the presence of chymotrypsin like endopeptidase.

The Enzymes: Chymotrypsin-Like Endopeptidase—

Chymotrypsin (EC 3.4.21.4) is a serine protease that preferentially cleaves peptide amide bonds where the carboxyl side of the amide bond (the $P_1$ position) is a tyrosine, tryptophan, or phenylalanine. Chymotrypsin also hydrolyzes other amide bonds in peptides at slower rates, particularly those containing leucine at the $P_1$ position By "chymotrypsin-like endopeptidase" it is meant an enzyme having an activity similar to that of mammalian chymotrypsin, e.g., chymotrypsin extracted from porcine pancreatic tissue. It is also meant an enzyme that has a higher specificity for cleaving at the carboxy-terminal side of each of tyrosine, phenylalanine, tryptophan, leucine, methionine and histidine residues than for cleaving on the carboxy-terminal side of both of arginine and lysine.

The chymotrypsin-like endopeptidase of the invention may be derived from a gram-positive bacterial strain such as *Bacillus, Clostridium, Enterococcus, Geobacillus, Kutzneria, Lactobacillus, Lactococcus, Oceanobacillus, Staphylococcus, Streptococcus,* or *Streptomyces* or a gram negative bacterial strain such as *Campylobacter, Escherichia* (preferably *E. coli*), *Nocardiopsis, Flavobacterium, Fusobacterium, Helicobacter, Ilyobacter, Neisseria, Pseudomonas, Salmonella,* or *Ureaplasma,* or a fungal strain such as *Saccharomyces, Kluyveromyces, Pichia, Candida, Aspergillus, Penicillium, Fusarium,* and *Claviceps*. Preferably, the chymotrypsin-like endopeptidase of the invention may be derived from gram positive or gram negative bacterial strains. In a more preferred embodiment, the chymotrypsin is derived from a strain of *Nocardiopsis,* preferably from *Nocardiopsis* sp. EMBL CDS CAI94179. In another preferred embodiment, the chymotrypsin-like endopeptidase has a sequence identity to the polypeptide EMBL CDS CAI94179 of at least 70%, at least 75%, at least 80%, at least 85%, at least 90%, at least 95%, at least 96%, at least 97%, at least 98%, at least 99%, or 100%.

In another more preferred embodiment, the chymotrypsin-like endopeptidase is derived from *Metarhizium,* preferably *Metarhizium anisopliae,* e.g. having the amino acid sequence of the mature polypeptide of the sequence TREMBL:Q9Y843. In another preferred embodiment, the chymotrypsin-like endopeptidase has a sequence identity to the polypeptide TREMBL:Q9Y843 of at least 70%, at least 75%, at least 80%, at least 85%, at least 90%, at least 95%, at least 96%, at least 97%, at least 98%, at least 99%, or 100%. In another more preferred embodiment, the chymotrypsin-like endopeptidase is derived from *Brachysporiella,* preferably *Brachysporiella gayana,* CGMCC 0865 (SEQ ID NO: 2 hereby incorporated by reference), amino acids 1-186 disclosed in WO2004/072279 hereby incorporated by reference. In another preferred embodiment, the chymotrypsin-like endopeptidase has a sequence identity to the latter polypeptide of reference of at least 70%, at least 75%, at least 80%, at least 85%, at least 90%, at least 95%, at least 96%, at least 97%, at least 98%, at least 99%, or 100%.

The concentration of the chymotrysin-like endopeptidase is preferably 100-100,000 USP Chymotrypsin Units per g milk-based protein, more preferably 500-50,000, and most preferably 1,000-20,000. One USP Chymotrypsin Unit is the activity causing a change in absorbance at 237 nm of 0.0075 at pH 7.0 and 25° C. using N-acetyl-L-tyrosine ethyl ester (ATEE) as substrate. Otherwise expressed this in terms of mg of >95% pure enzyme protein/ml, this means that the chymotrysin-like endopeptidase concentration can range from 0.05 to 2, preferably from 0.1 to 1, and more preferably 0.15 to 0.4 mg per gram of milk protein. This is independent of the presence of trypsin-like endopeptidase During the hydrolysis process the enzymes are used together as a mixture. For example the trypsin-like endopeptidase derived from *Kutzneria albida* may be combined with chymotrypsin-like endopeptidase from *Nocardiopsis* sp or from *Metarhizium anisopliae* or from *Brachysporiella gayana*. For example, the trypsin-like endopeptidase derived from *Fusarium oxysporum* may be combined with chymotrypsin-like endopeptidase from *Nocardiopsis* sp or from *Metarhizium anisopliae* or from *Brachysporiella gayana*.

The inventers have found that the ratio of trypsin-like endopeptidase to chymotrysin-like endopeptidase (T/C ratio) based on weight of enzyme should be in the range 5:1 to 35:1, preferably 20:1 to 30:1, more preferably 27:1. Furthermore, when the trypsin-like endopeptidase is derived from a strain of *Fusarium* and chymotrysin-like endopeptidase is derived from the strain *Nocardiopsis* a preferred range for the T/C ratio is 8:1 to 11:1, more preferably 9:1.

This is particularly true for trypsin-like endopeptidase (T) from *Fusarium oxysporum* combined with chymotrypsin-like endopeptidase (C) from *Nocardiopsis* in T/C a ratio of 9:1, the trypsin-like endopeptidase (T) from *Kutzneria albida* combined with chymotrypsin-like endopeptidase (C) from *Nocardiopsis* in T/C a ratio of 27:1 and trypsin-like endopeptidase (T) from *Fusarium oxysporum* combined with chymotrypsin-like endopeptidase (C) from *Nocardiopsis* in T/C a ratio of 27:1.

The Hydrolysis Process:

The typical conditions for carrying out the hydrolysis process have been described in the prior art. The temperature may range from about 40° C. to 60° C., preferably at 50° C., the reaction time from 1 to 6 hours, preferably 4 hours, and pH values may fall within the range 6.5 to 8.5, preferably 7.0 to 8.0. The pH may be adjusted with known agents, for example $Ca(OH)_2$. In documents U.S. Pat. No. 5,039,532 or EP0631731A1 is described a two-step hydrolysis reaction with a heat denaturation step in between to insure that the final hydrolysate is substantially free of milk protein allergens. The heat denaturation step is preferably carried out at 95° C. for 5 minutes.

Optionally the milk-based protein solution or suspension may be pre-heated (for example to 80-100° C. for 5-30 minutes, or for 130° C. for about 30-60 seconds) to ensure denaturation of whey proteins, e.g. α-lactalbumin, β-lactoglobulin and serum albumin (BSA).

Irrespective of how the hydrolysis is carried out, the hydrolysis product undergoes a heat treatment, which inactivates the enzyme carrying out the hydrolysis. This heat treatment comprises preheating the hydrolysate to a temperature of or above 75° C., and keeping it at that temperature (preferably at 75° C.-85° C.) for about 0.1 to 30 minutes to promote auto-digestion of the enzyme, this treatment advantageously being followed by sterilization, preferably at ultra-high temperature, for example at 125° C.-135° C. for 30 seconds to 3 minutes, by injection of steam or in a heat exchanger.

The hydrolysate thus obtained may be clarified, filtered or ultrafiltrated. It may also be concentrated. It may then be dried, for example by lyophylisation, spray drying, or by freeze drying for different applications, or may even be subsequently treated. In the latter case, the enzyme may be inactivated during the subsequent treatment.

The hydrolysates of the invention may have an extent of hydrolysis that is characterised by NPN/TN %. NPN/TN % means the Non protein nitrogen divided by the total nitrogen×100. The non protein nitrogen is amino nitrogen that is free to react with a reagent such as trinitrobenzenesulfonic acid (TNBS). NPN/TN % may be measured as detailed in Adler-Nissen J-, 1979, *J. Agric. Food Chem.*, 27 (6), 1256-1262. In general, extensively hydrolysates are characterised as having a NPN/TN % of greater than 95%, whereas a partially hydrolysed hydrolysate is characterized as having a NPN/TN % in the range 75%-85%. In a preferred embodiment the hydrolysates of the invention have an NPN/TN % in the range of 70-90%, preferably 75 to 85%. The latter hydrolysates are "partial" hydrolysates. These hydrolysates may also be characterised in that 60-70% of their protein/peptide population has a molecular weight of <1000 Daltons In another preferred embodiment where "extensive" hydrolysates are desired the hydrolysates of the invention have an NPN/TN % in the range of greater than 95%. These hydrolysates may also be characterised in that at least 95% their protein/peptide population has a molecular weight of <1000 Daltons.

The hydrolysates of the invention may have an extent of hydrolysis that is characterised by NPN/TN %. Non-Protein Nitrogen over Total Nitrogen is widely used as a measure of soluble peptides created by enzymatic hydrolysis. The analytical method used to measure the NPN is equivalent to the AOAC method 991.21. In the 100% whey protein based hydrolysates, the NPN/TN content typically ranges between 70-90%. In a preferred embodiment the hydrolysates of the invention have an NPN/TN % in the range of 70-90%, preferably 75 to 85%. In another preferred embodiment where an extensively hydrolysed hydrolysate is desired the hydrolysates of the invention have an NPN/TN % in the range of greater than 95%.

The molecular weight distribution of the peptides in the protein hydrolysate obtained may be determined, e.g., by size exclusion chromatography (SEC). In a preferred embodiment, the hydrolysate of the invention is a partial hydrolysate and is comprised of peptides where less than 1% on a weight-basis has a molecular weight of above 20,000 kDa. In a more preferred embodiment the hydrolysates of the invention have a peptide weight distribution similar to that obtained with mammalian enzyme, specifically porcine enzyme for example PTN 6.0S® (also known as PTN) from Novozyme (Denmark) (see example 1 FIG. 1). This reference enzyme is a trypsin extracted from pig pancreas that contains trypsin as the main component but also residual chymotrypsin. It has a trypsin activity of 1350 USP trypsin/g, and Chymotrypsin activity of 80 activities USP chymotrypsin/g. This leads to a T/C ratio of 16 based on activities.

The enzyme specificity of the enzyme mixtures used during the hydrolysis may be evaluated by sequencing the peptides comprised in the resultant hydrolysate. The peptide sequences are identified by LC-MS/MS. In a more preferred embodiment the hydrolysates of the invention have an enzyme specificity close to that obtained with mammalian enzyme, specifically porcine enzyme for example PTN 6.0S described above (see Example 1 FIG. 2).

The hydrolysis efficiency may be evaluated by measuring alkali (OH) consumption during hydrolysis. In a more preferred embodiment, the hydrolysates of the invention have an hydrolysis performance close to that obtained with mammalian enzyme, specifically porcine enzyme, for example PTN described above (see Example 1 FIG. 3).

The residual antigenicity of the hydrolysates may be evaluated using standard immunoassays such ELISA tests. Preferably the hydrolysates of the invention present a residual β-lactoglobulin (BLG) of <3 mg BLG equivalent/g protein equivalent, more preferably <2 mg BLG equivalent/g protein equivalent, most preferably <1 mg BLG equivalent/g protein equivalent (see example 1).

The hydrolysates of the invention may be incorporated into infant formula, follow-on formula, a baby food, infant cereals, growing-up milk, infant or child's food supplement or an adult nutritional composition, i.e. all preparations targeting prevention or treatment of allergy, as well as any other benefits that protein hydrolysates could provide to humans, and, preferably, said composition is a starter infant formula.

In one embodiment of the invention, the hydrolysates of the invention are used in combination with selected probiotics, for example in infant formula. The selected probiotics can be any of the probiotics conventionally used in infant formula. Preferably the probiotics are those able to provide an additional or synergistics effect on allergies and/or induction of oral tolerance and/or inflammatory processes.

Examples of suitable probiotic micro-organisms which may be used in the present invention include yeasts such as *Saccharomyces*, *Debaromyces*, *Candida*, *Pichia* and *Torulopsis*, moulds such as *Aspergillus*, *Rhizopus*, *Mucor*, and *Penicillium* and *Torulopsis* and bacteria such as the genera *Bifidobacterium*, *Bacteroides*, *Clostridium*, *Fusobacterium*, *Melissococcus*, *Propionibacterium*, *Streptococcus*, *Enterococcus*, *Lactococcus*, *Staphylococcus*, *Peptostrepococcus*, Bacillus, Pediococcus, Micrococcus, Leuconostoc, Weissella, Aerococcus, Oenococcus and Lactobacillus. Specific examples of suitable probiotic micro-organisms are: Saccharomyces cereviseae, Bacillus coagulans, Bacillus licheniformis, Bacillus subtilis, Bifidobacterium bifidum, Bifidobacterium infantis, Bifidobacterium longum, Enterococcus faecium, Enterococcus faecalis, Lactobacillus acidophilus, Lactobacillus alimentarius, Lactobacillus casei subsp. casei, Lactobacillus casei Shirota, Lactobacillus curvatus, Lactobacillus delbruckii subsp. lactis, Lactobacillus farciminus, Lactobacillus gasseri, Lactobacillus helveticus, Lactobacillus johnsonii, Lactobacillus reuteri, Lactobacillus rhamnosus (Lactobacillus GG), Lactobacillus sake, Lactococcus lactis, Micrococcus varians, Pediococcus acidilactici, Pediococcus pentosaceus, Pediococcus acidilactici, Pediococcus halophilus, Streptococcus faecalis, Streptococcus thermophilus, Staphylococcus carnosus, and Staphylococcus xylosus.

Preferred probiotic bacterial strains include *Lactobacillus rhamnosus* ATCC 53103 obtainable from Valio Oy of Finland under the trade mark LGG, *Lactobacillus rhamnosus* CGMCC 1.3724, *Lactobacillus paracasei* CNCM 1-2116, *Lactobacillus reuteri* ATCC 55730 and *Lactobacillus reuteri* DSM 17938 obtainable from BioGaia AB, *Bifidobacterium lactis* CNCM 1-3446 sold inter alia by the Christian Hansen company of Denmark under the trade mark Bb 12 and *Bifidobacterium longum* ATCC BAA-999 sold by Morinaga Milk Industry Co. Ltd. of Japan under the trade mark BB536.

If present in the compositions of the present invention, the probiotics are preferably present in an amount of $10^3$ to $10^{12}$ cfu/g, more preferably $10^6$ to $10^{11}$ cfu/g, even more preferably $10^4$ to $10^9$ cfu/g, most preferably $10^7$ to $10^9$ cfu/g composition or per mL of composition.

EXAMPLES

Example 1

A series of hydrolysis reactions were carried out using the same milk protein substrate and a set of 6 enzyme solutions, consisting of one standard PTN solution and five different mixtures of trypsin and chymotrypsin-like endopeptidases according to Table 1. The starting material was 500 ml of an 8% solution of substrate milk protein MWP28/DWP28 in a ratio 83/17 based on protein weight. The final composition for the substrate is 27.7% total solids, 8% protein, and 18.48% lactose.

The protein substrate was dissolved as an 8% solution w/v in water. For the reaction, a total volume of 500 ml was used. The temperature was equilibrated to 55° C. The pH was then adjusted to pH 7.4 using 10% $Ca(OH)_2$ solution. After enzyme addition (half of the total useful Enzyme for $1^{st}$ hydrolysis step), the pH was maintained constant at pH 7.4 by addition of 0.25M NaOH using an Autotitrator DL50 Graphix (Mettler Toledo during 4 h at 55° C. The hydrolysate was heated for 5 min at 93° C. After equilibration of temperature to 55° C., additional enzyme was introduced (half of the total enzyme for $2^{nd}$ hydrolysis step) and pH was maintained as above. After 2 hours of hydrolysis, the enzymatic reaction was stopped by heat treatment (5 min at 85° C.) to inactivate the enzymes.

Table 1 shows the series of experiments carried out with the various ratios of enzymes. TL1 and TL2 denote the trypsin-like endopeptidases from *Fusarium oxysporum*, and *Kutzneria albida* respectively. CTL2 and CTL3 denote the chymotrypsin-like endopeptidases from *Metarhizium anisopliae* and *Nocardiopsis* sp respectively

| Experiment | Enzyme (mg/g protein) | T/CRatio (w/w) |
|---|---|---|
| No 1 | PTN | 16* |
| No 2 | TL1 + CTL3 (1.8 + 0.2) | 9 |
| No 3 | TL2 + CTL3 (1.8 + 0.3) | 6 |
| No 4 | TL2 + CTL3 (2.7 + 0.1) | 27 |
| No 5 | TL2 + CTL2 (1.8 + 0.6) | 3 |
| No 6 | TL1 + CTL3 (2.7 + 0.1) | 27 |

16* ratio is based on enzyme activity

Figure 2:
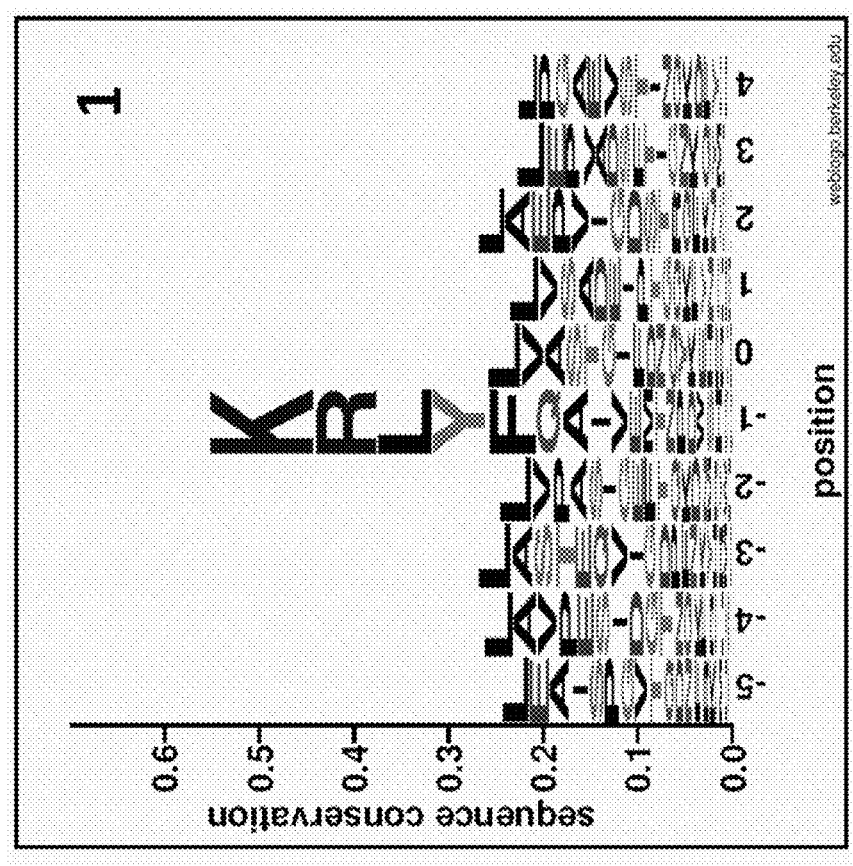
FIG. 2 Enzyme specificity analysis of the hydrolysates of Example 1. Peptide sequences are identified by LC-MS/MS (LTQ-Orbitrap MS with Allegro HPLC pumps from Thermo Scientific)). For each identified sequence, the five amino acids before and after the cleavage site (position −1) are extracted, and a frequency plot (or sequence conservation plot) is built. Amino acids are plotted from highest (top) to lowest (bottom) frequency with their vertical size being proportional to their frequency. Results show that the enzyme mixtures used in experiment 4 and 6 have an enzyme specificity that is comparable to the reference PTN (experiment 1).
Figure 2:
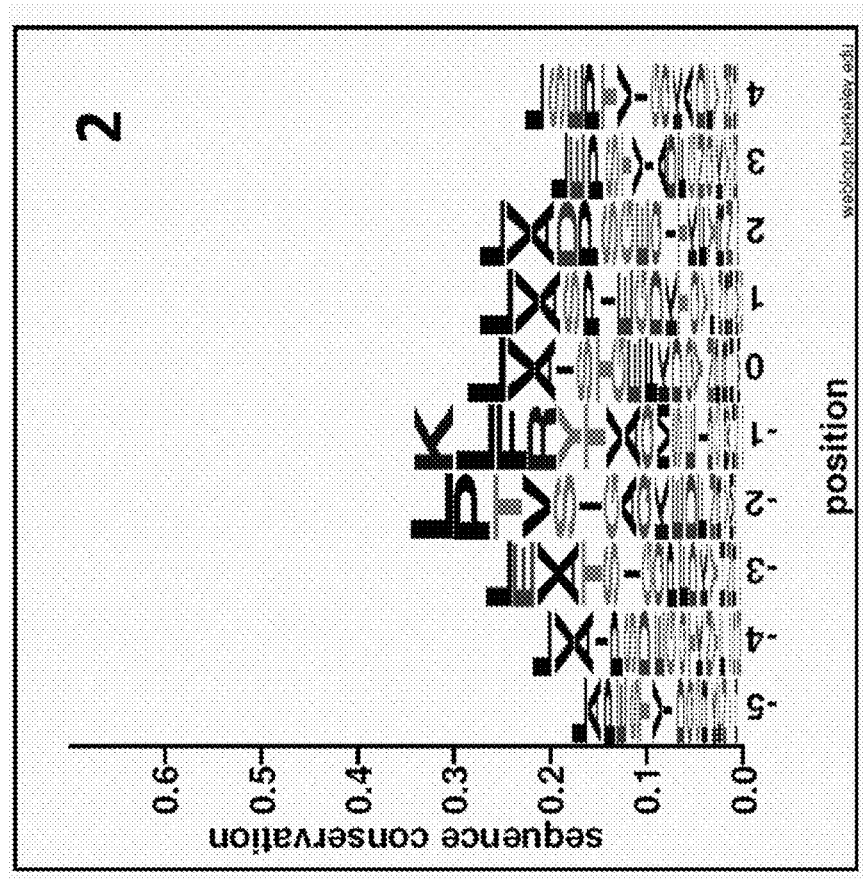
Figure 2:
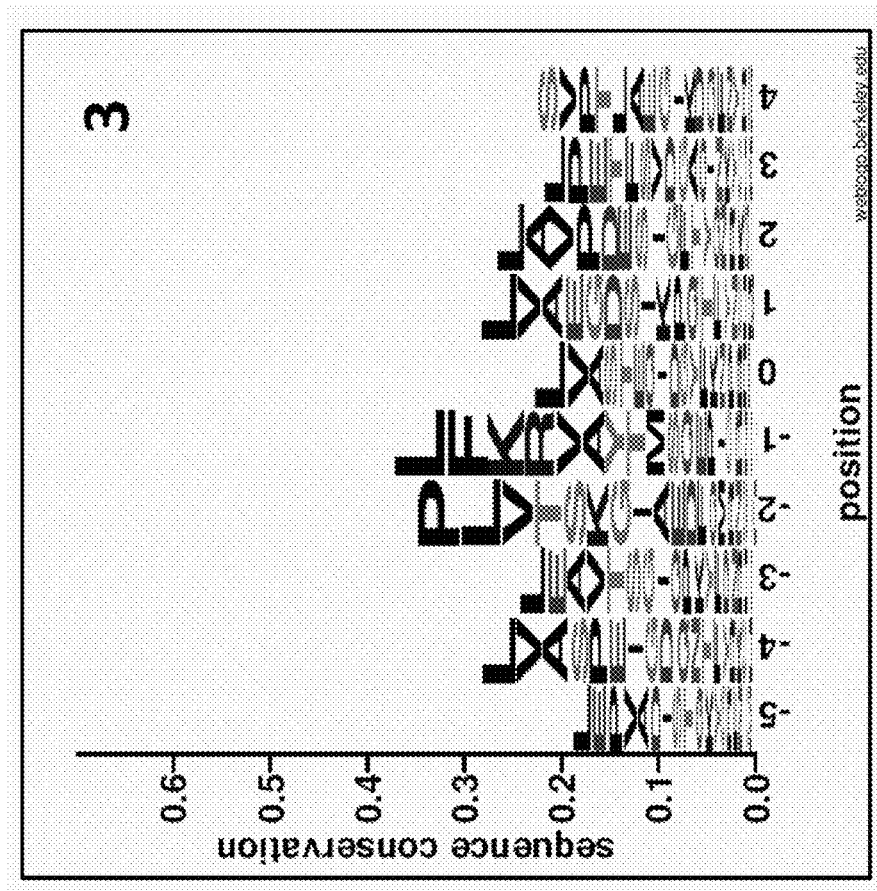
Figure 2:
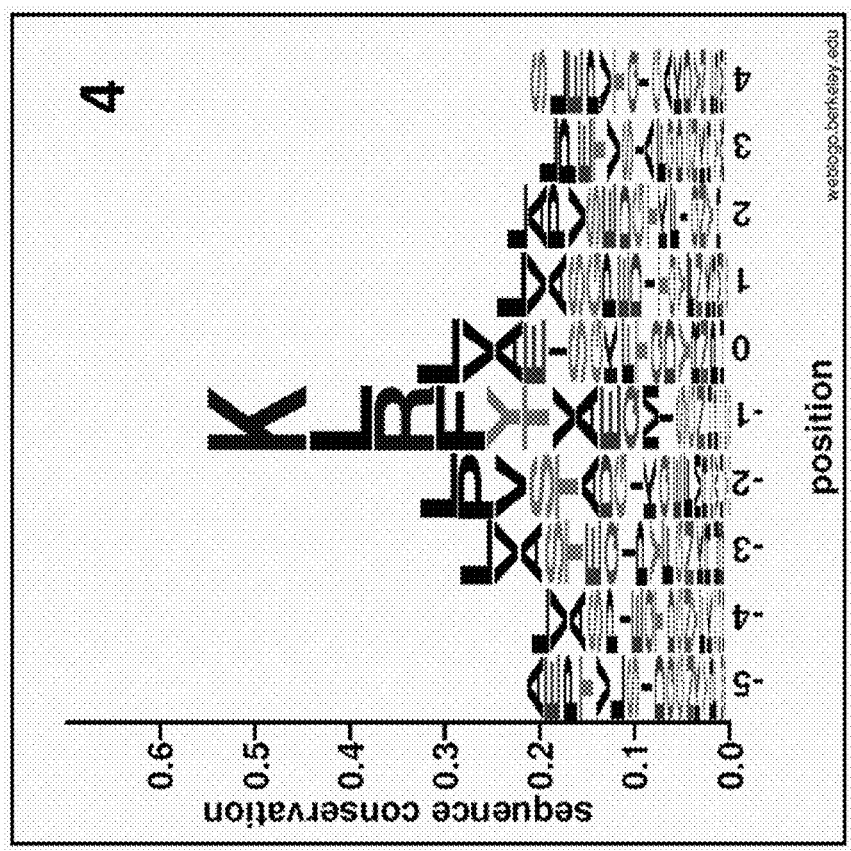
Figure 2:
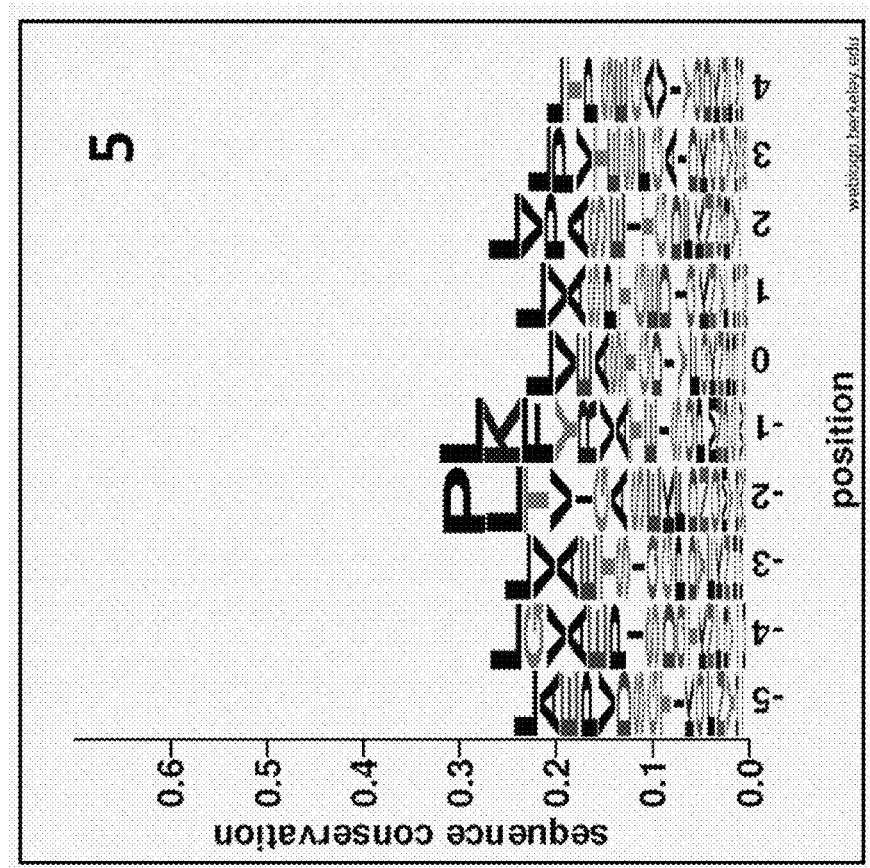
Figure 2:
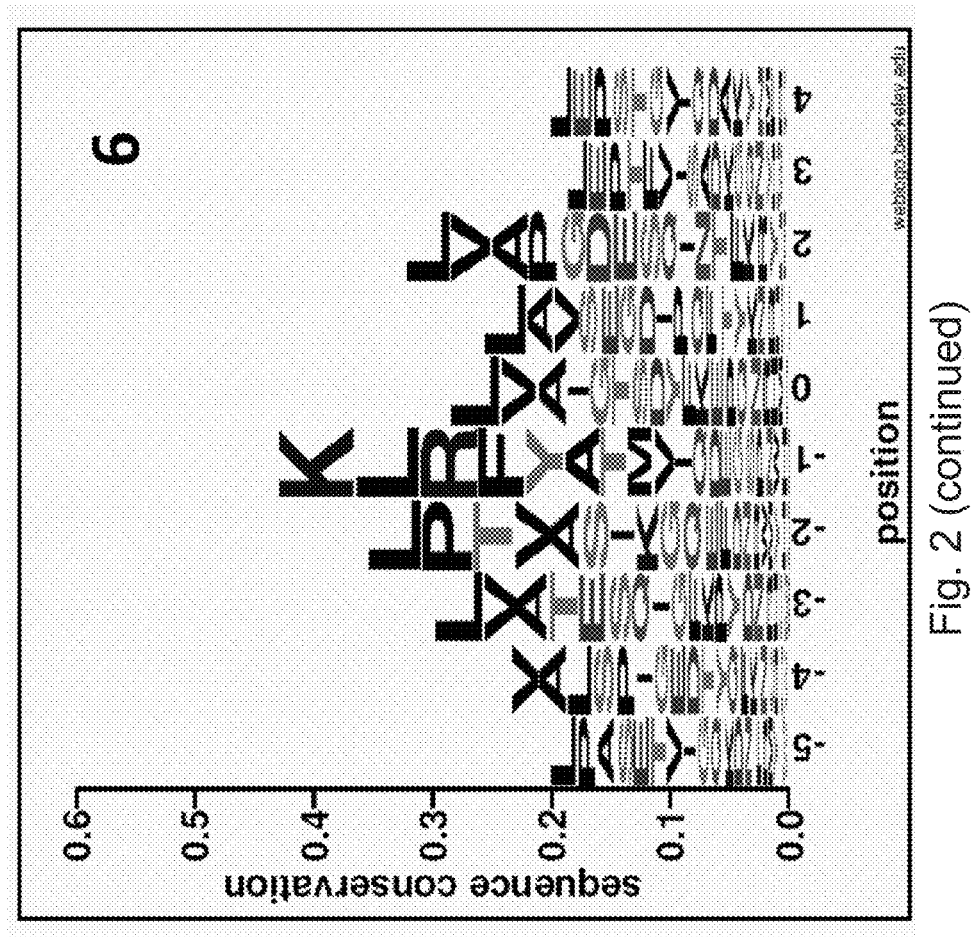
Figure 3:
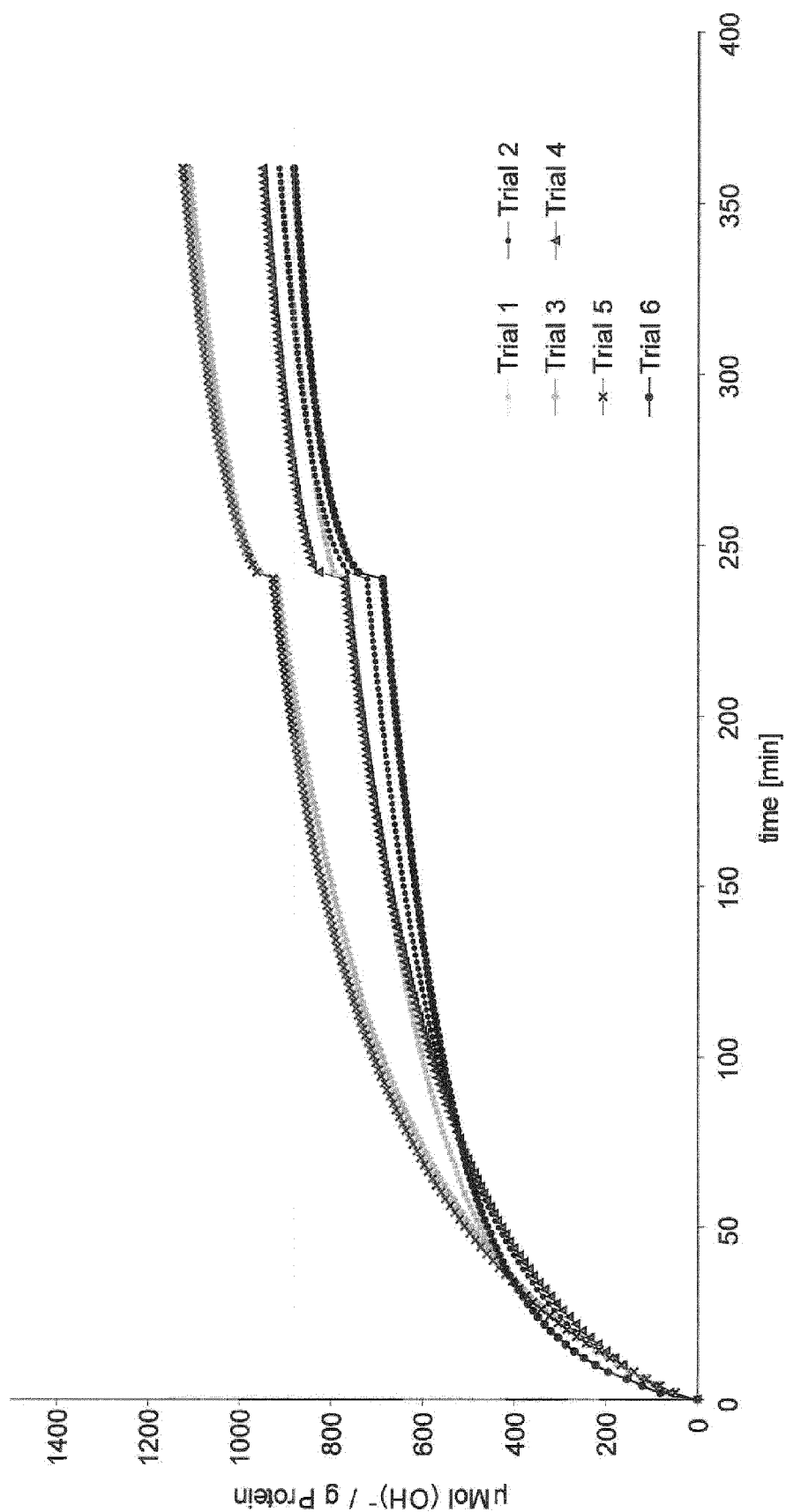
FIG. 3 Kinetics of OH— consumption during hydrolysis reactions of Example 1 (µmole OH— consumed/g protein).

The six hydrolysates produced were analysed using three different methods, peptide size exclusion chromatography, enzyme specificity analysis, and residual antigenicity. The hydrolysis efficiency of the six reactions was analysed by monitoring OH— consumption. The results are shown in FIGS. 1-3 respectively.

Antigenicity: The residual antigenicity of the hydrolysates was tested using a commercial enzyme immunoassay (RIDASCREEN β-Lactoglobulin (BLG), r-biopharm), which is designed to quantify native and processed residual β-lactoglobulin in food products. The microtiter wells are coated with BLG. Standards, sample solutions and anti-BLG antibodies are added. Free and immobilized BLG compete for the antibody binding sites. After washing, secondary antibodies labelled with peroxidase are added and bind to the antibody-BLG-complexes. Any unbound enzyme conjugate is then removed by a washing step. Enzyme substrate and chromogen are added to the wells. Bound enzyme conjugate converts the colourless chromogen into a coloured product. The measurement is made photometrically and the absorption is inversely proportional to the BLG concentration in the sample.

The six hydrolysates tested in example 1 all presented a residual β-lactoglobulin (BLG) of less than 0.85 mg BLG equivalent/g protein equivalent. This is far below the level at which one can declare infant formula hypoallergenic as indicated by the European directive 2006/125/CE on infant formulas published 5 Dec. 2006, JO Dec. 6, 2006 L339/16. The directive requires that the immunoreactive protein be less than 1% of the total nitrogen containing substances. This is equivalent to 3 mg residual β-lactoglobulin (BLG/g protein equivalent). BLG constitutes somewhere between 30% to 50% of the total immunoreactive material in whey. Thus a BLG level below 3 mg residual β-lactoglobulin/g protein equivalent indicates that the product has no more than 1% immunoreactive protein. Such level is consistent with Annex IV of European Commision Directive 2006/125/CE which sets forth certain conditions for an infant formula claiming to reduce the risk of allergy.

CONCLUSION

A number of mixtures of trypsin-like endopeptidases and chymotrypsin-like endopeptidases from microbial sources have been identified as being suitable for producing milk protein hydrolysates with similar properties to those of the milk hydrolysates produced by mammalian enzymes. The inventers have carried out a range of experiments to evaluate the optimal ratio of enzymes to provide hydrolysates with the desired physical, chemical and biological properties. The bacterial source and ratio of trypsin-like endopeptidases to chymotrysin-like endopeptidases (based on weight of enzyme) as well as the enzyme to protein substrate ratio and temperature were varied.

A mixture of a trypsin-like endopeptidase from *Fusarium oxysporum* or *Kutzneria albida* combined with a chymotrypsin-like endopeptidase from *Nocardiopsis sp* or *Metarhizium anisopliae* are found to be good candidates to replace the mammalian enzymes currently used. The mixtures of the invention, especially when the try psi n-like endopeptdase and chymotrypsin-like endopeptidase are used in specific ratios, have been clearly shown to provide peptide profiles very similar to those produced with the mammalian enzymes.

This is particularly true for trypsin-like endopeptidase (T) from *Fusarium oxysporum* combined with chymotrypsin-like endopeptidase (C) from *Nocardiopsis* in T/C a ratio (based on enzyme weight) of 9:1, and for the trypsin-like endopeptidase (T) from *Kutzneria albida* combined with chymotrypsin-like endopeptidase (C) from *Nocardiopsis* in T/C a ratio of 27:1 and for the trypsin-like endopeptidase (T) from *Fusarium oxysporum* combined with chymotrypsin-like endopeptidase (C) from *Nocardiopsis* in T/C a ratio of 27:1.

The hydrolysates thus produced present low allergenicity. They may reduce the risk of allergies later in life and are may be suitable for incorporation into an infant formula and/or a nutritional composition that are targeted to healthy individuals at risk of allergies. They are suitable for the incorporation into any kind of food supplements for adults or children or babies. They may also have the capacity to induce oral tolerance.

Apart from the allergy prevention aspect, mixtures of trypsin and chymotrypsin from microbial sources may be used to produce therapeutic products, such as those intended to feed allergic subjects. They may also be used to produce any kind of protein hydrolysates targeting other benefits than prevention/treatment of allergy.

The invention claimed is:

1. A method for the induction of oral tolerance in infants or patients in need thereof, the method comprising:
    treating a milk-based proteinaceous material with at least one trypsin-like endopeptidase derived from a strain of *Kutzneria*, and at least one chymotrypsin-like endopeptidase derived from a microorganism, the ratio of the trypsin-like endopeptidase to the chymotrypsin-like endopeptidase being between 20:1 to 35:1 based on weight of enzyme; and
    administering a composition comprising milk-based protein hydrolysate obtained by the treated milk-based proteinaceous material.

2. The method according to claim 1, wherein the at least one trypsin-like endopeptidase has at least 75% sequence identity to the mature polypeptide SEQ ID NO:1.

3. The method according to claim 1, wherein the at least one chymotrypsin-like endopeptidase is derived from a strain of *Nocardiopsis*.

4. A method for reducing the risk of allergies in infants, the method comprising:
    treating a milk-based proteinaceous material with at least one trypsin-like endopeptidase produced from a strain of *Kutzneria*, and at least one chymotrypsin-like endopeptidase produced from a microorganism, the ratio of the trypsin-like endopeptidase to the chymotrypsin-like endopeptidase being between 20:1 to 35:1 based on weight of enzyme; and
    administering a composition comprising milk-based protein hydrolysate obtained by the treated milk-based proteinaceous material.

5. The method according to claim 4, wherein the chymotrypsin-like endopeptidase is derived from a strain of *Nocardiopsis*.

6. The method according to claim 4, wherein the chymotrypsin-like endopeptidase has at least 75% sequence identity to and SEQ ID NO: 2 (CGMCC 0865, amino acids 1-186).

* * * * *